United States Patent [19]

Eenboom et al.

[11] 4,446,453

[45] May 1, 1984

[54] METHOD FOR THE REGISTRATION AND EVALUATION OF DENTAL FINDINGS AS WELL AS AN APPARATUS FOR THE IMPLEMENTATION OF THE METHOD

[75] Inventors: Algund Eenboom, Leer; Edzard Müller, Hinte, both of Fed. Rep. of Germany

[73] Assignee: Fried. Krupp GmbH, Essen, Fed. Rep. of Germany

[21] Appl. No.: 247,301

[22] PCT Filed: Jul. 23, 1980

[86] PCT No.: PCT/DE80/00105

§ 371 Date: Mar. 18, 1981

§ 102(e) Date: Mar. 18, 1981

[87] PCT Pub. No.: WO81/00201

PCT Pub. Date: Feb. 5, 1981

[30] Foreign Application Priority Data

Jul. 25, 1979 [DE] Fed. Rep. of Germany ....... 2930142

[51] Int. Cl.³ .............................................. G09G 3/00
[52] U.S. Cl. ............................. 340/286 M; 340/700; 340/525; 434/263; 235/383; 433/25
[58] Field of Search ............... 340/700, 723, 724, 524, 340/525, 286 M, 815.21, 815.23; 356/237; 433/25, 26, 27, 215; 434/263; 235/375, 383

[56] References Cited

U.S. PATENT DOCUMENTS

| 3,679,875 | 7/1972 | Rawson et al. | 235/383 |
|---|---|---|---|
| 3,741,471 | 6/1973 | Mani | 235/61.9 R |
| 3,771,156 | 11/1973 | Watts et al. | 340/286 M |
| 3,943,914 | 3/1976 | Grenfell et al. | 433/215 |
| 4,101,883 | 7/1978 | Hempenius et al. | 340/286 M |
| 4,184,175 | 1/1980 | Mullane, Jr. | 358/93 |
| 4,268,744 | 5/1981 | McGeary | 235/375 |
| 4,345,132 | 8/1982 | Takase et al. | 235/375 |

FOREIGN PATENT DOCUMENTS

| 518671 | 2/1931 | Fed. Rep. of Germany | 434/263 |
|---|---|---|---|
| 862381 | 1/1953 | Fed. Rep. of Germany | |
| 2164405 | 7/1973 | France | |

OTHER PUBLICATIONS von T. Oguma, Ein Neues Elektronisches Evolventen--Prüfgerät, ("A New Electronic Involute Monitor"), 1972, pp. 445-446.

Primary Examiner—Marshall M. Curtis
Attorney, Agent, or Firm—Spencer & Frank

[57] ABSTRACT

A method for the registration and evaluation of dental findings corresponding to dental examination points. The method is carried out with an evaluation apparatus including a marking apparatus having spatial allocations corresponding to each examination point and a marking element associated with each spatial allocation. The method comprises the steps of examining the points, one after the other, in a predetermined order to obtain respective dental findings; entering the finding corresponding to each examination point into the evaluation apparatus; and marking the finding of each examination point in the corresponding spatial allocation on the marking apparatus by use of the associated marking element.

15 Claims, 13 Drawing Figures

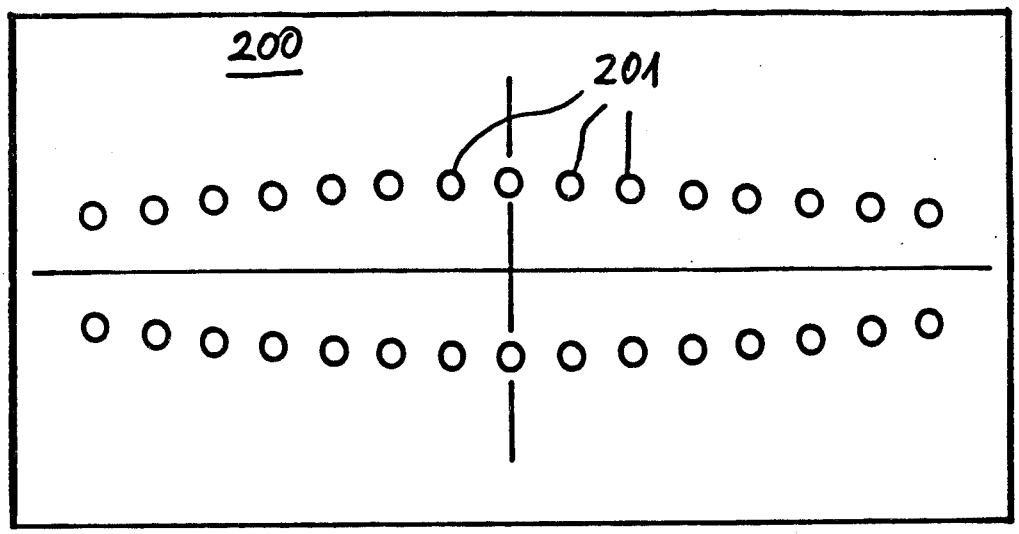
FIG 7
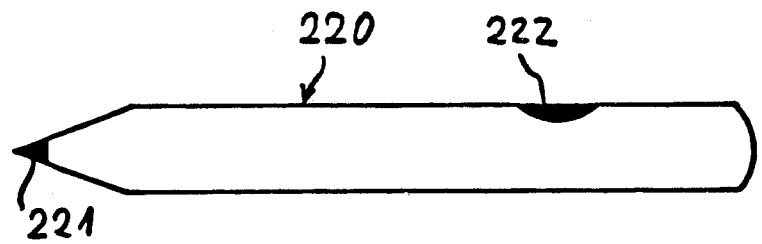
FIG 8
FIG 9
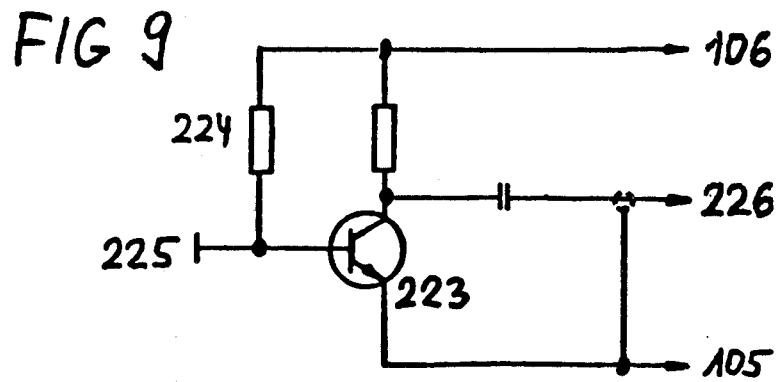

METHOD FOR THE REGISTRATION AND EVALUATION OF DENTAL FINDINGS AS WELL AS AN APPARATUS FOR THE IMPLEMENTATION OF THE METHOD

BACKGROUND OF THE INVENTION

The invention relates to a method for the registration and evaluation of dental findings as well as to an apparatus for the implementation of the method.

In order to control the mouth hygiene during a systematic periodontal treatment a repeated exact registration of dental findings of possibly existing dental film (plaque) is absolutely essential. To achieve this, a visual determination and a manually drawn-up registration of the plaque findings, as practised up to now, no longer satisfy the requirements for a consistent periodontal treatment moreover, the diagnosis practised so far is comparatively inefficient and time-consuming, and a possible record of the findings does not comprise the desirable informative effect, especially not for the patient, and offers only little motivating incentive for further dental care.

SUMMARY OF THE INVENTION

It is an object of the present invention to provide a method that, on the one hand, can be implemented with little expense in time and personnel and that is, on the other hand, suited to better explain the findings to the patient and motivate him at the same time to carry out an effective dental care.

These and other objects are accomplished in accordance with the invention in which a method is provided for the registration and evaluation of dental findings corresponding to dental examination points. The method is carried out with an evaluation apparatus including a marking apparatus having spatial allocations corresponding to each examination point and a marking element associated with each spatial allocation. The method includes the steps of examining the points, one after the other, in a predetermined order to obtain respective dental findings; entering the finding corresponding to each examination point into the evaluation apparatus; and marking the finding of each examination point in the corresponding spatial allocation on the marking apparatus by use of the marking element.

The method proposed allows for the implementation of recording examination findings with lower expenditure in personnel and time and offers, above all, the possibility to illustrate in an impressive manner the record of the findings to the patient. The optical markings may be achieved either by electric lamps, one of which is allocated to each examination point and is lit up when the finding is positive and/or by a graphic representation.

It is advantageous to give the ratio of the number of the positive findings to the number of examination positions and to let the quotient thus reached appear on a display tableau as a so-called index (e.g. plaque index) in terms of percentage. The dentist, as well as the patient, are thereby in a position to observe the success of a periodontal treatment by means of the index.

BRIEF DESCRIPTION OF THE DRAWINGS

FIG. 7 shows a schematic view of a display tableau according to an improved version of the invention.

FIG. 8 illustrates a sensor head according to a further aspect of the invention.

FIG. 9 is a circuit diagram for an AF amplifier for a sensor head according to FIG. 8.

DETAILED DESCRIPTION OF THE PREFERRED EMBODIMENTS

Figure 1:
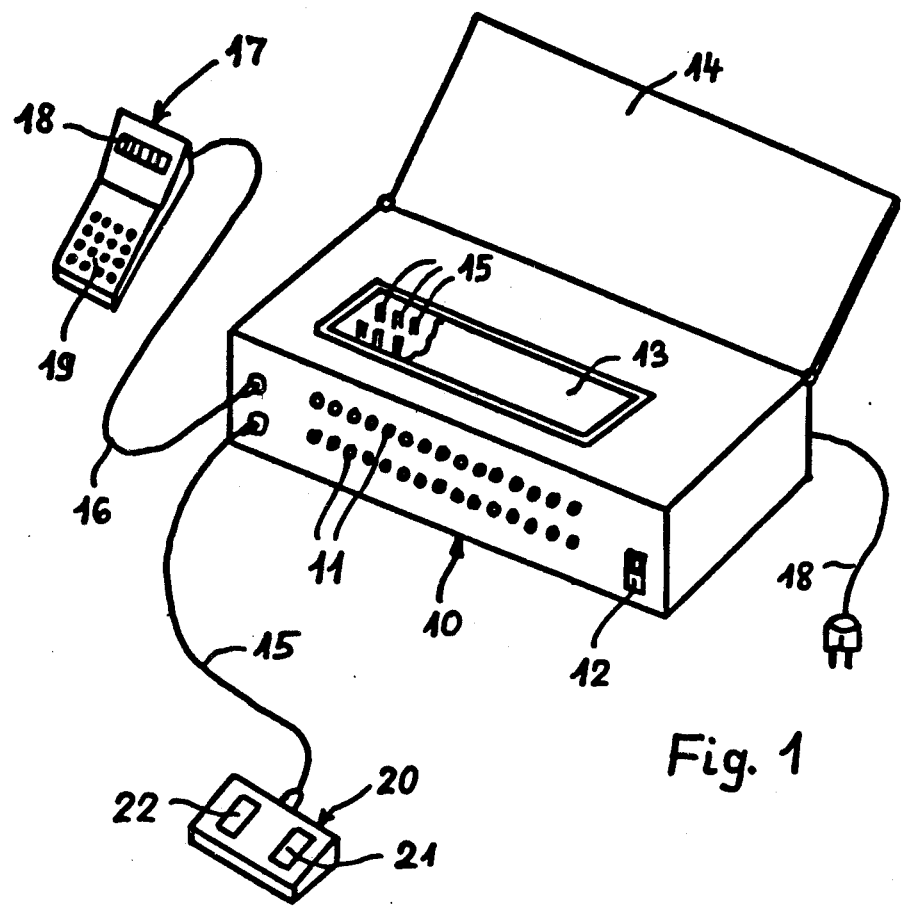
FIG. 1 is a schematic view of an apparatus for implementing the method according to the invention.

The arrangement shown in FIG. 1 consists of a registration apparatus 10 as well as a double foot switch 20 and a calculator 17, both connected to the apparatus 10. The registration apparatus 10 has a registration field 13 on its upper side comprising a plurality of heating elements 15. A registration carrier 30 (FIG. 2) can be placed onto this registration field and pressed down by a folding lid 14. The registration carrier consists of thermo-sensitive paper on which has been printed a dentition diagram of known arrangement. The position of the teeth of the four quadrants are labelled with numbers 1 to 8. The registration apparatus 10 further includes a field of LEDs (light emitting diodes) 11.

Figure 2:
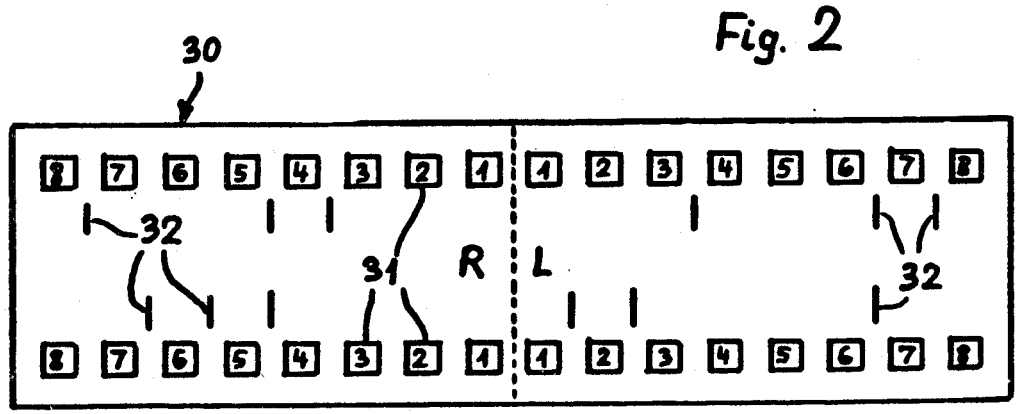
FIG. 2 is a registration carrier for the apparatus of FIG. 1.

The method as well as the apparatus according to the invention will now be described in connection with FIGS. 1 and 2. A registration carrier 30 is placed onto the registration field 13 and held in place by folding down lid 14. After actuation of power switch 12, the apparatus is in its starting position and a counter in the registration apparatus is also in its starting position. Now the patient's teeth are examined in a defined order for plaque in the interdental spaces. If the finding is positive, the positive switch 21 of foot switch 20 is actuated; if the finding is negative, the negative switch 22 is actuated. Actuation of one or the other of these two switches, 21 or 22, advances the counter into its first position, lighting the first light emitting diode 11. Operation of the positive switch causes a simultaneous actuation of the first of the heating elements 15 and produces thereby a mark 32 between teeth 8 and 7 in the upper left quadrant.

Each actuation of one or the other of switches 21 or 22 advances the counter by one position, and the corresponding LED indicates the corresponding serial position of the examination. If the positive switch is actuated the appropriate heating element 15 is energized and a mark printed at the corresponding mark position; if the negative switch is actuated no mark is printed at the corresponding marking position. This procedure is continued until the last marking position has been reached. The registration carrier 30 now clearly indicates at what positions plaque is existing, and this print-out may be compared with prints of further examinations. Moreover, the plaque index can be obtained by dividing the number of positive findings by the number of examination points.

Parallel to the marking of the registration carrier 30 at each positive finding, a counting pulse is fed through line 16 to the calculator 17, the display 18 of which will after termination of the examination indicate the number of positive findings. Subsequently this result is divided by the number of examination steps entered via keyboard 19, and the plaque index is obtained when the result of the division is given in terms of percentage.

In the following text the functioning of the circuit arrangement according to FIGS. 3 to 6 will be described. Please note that lines and terminals in the various Figures marked with identical numerals or letters are connected to each other.

Figure 3:
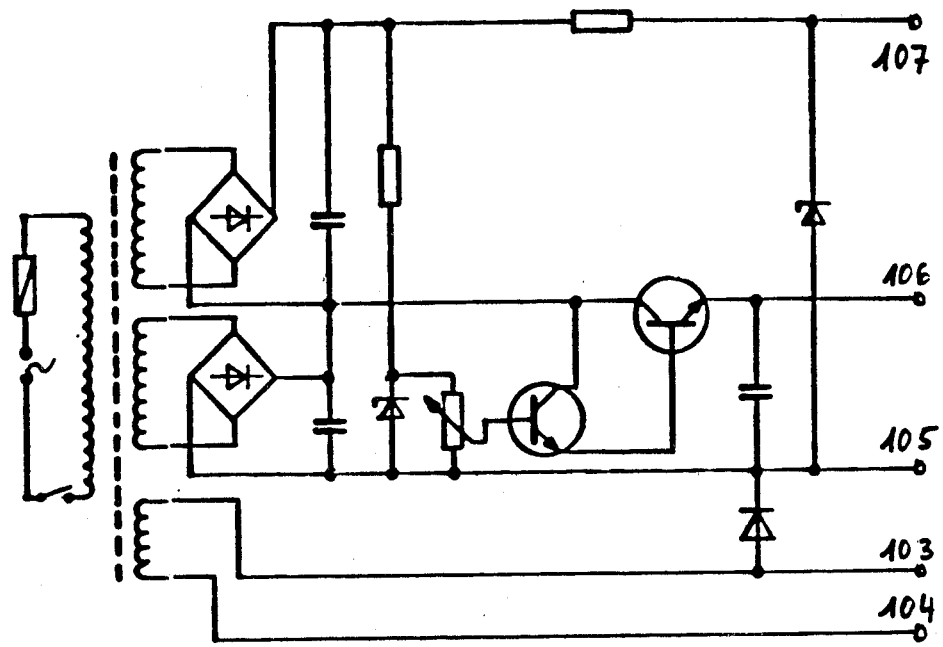
FIG. 3 is a circuit diagram for power supply for the apparatus of FIG. 1.

The power supply in FIG. 3 provides +9 volts dc at terminal 106, and +24 volts dc at terminal 107, both voltages being with respect to ground terminal 105. Terminals 103, 104 provide 3 volts ac for the heating elements 15.

Figure 4:
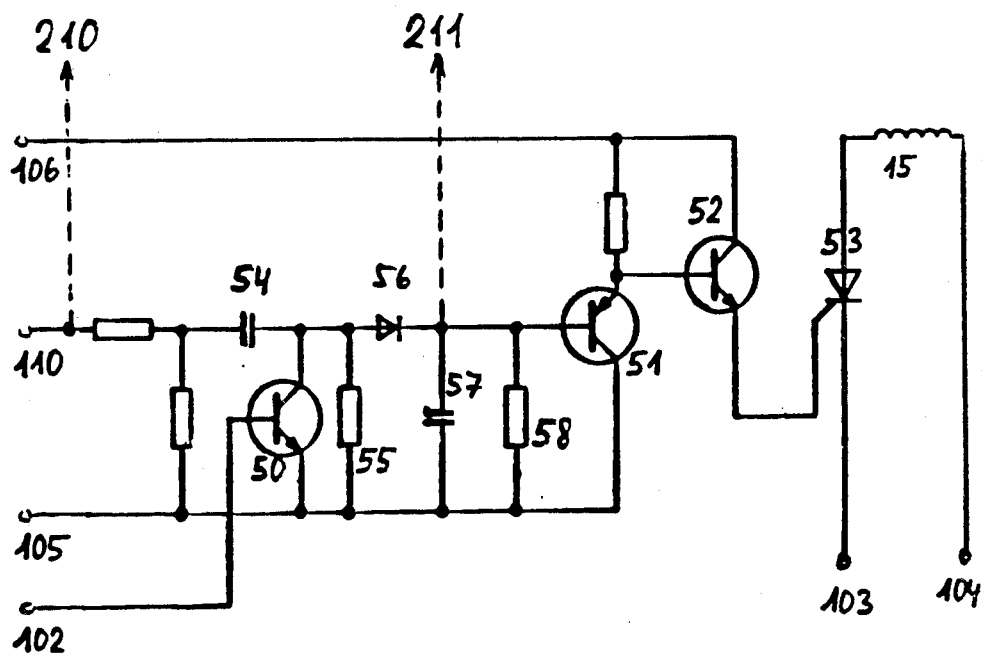
FIG. 4 is a circuit diagram for switching amplifier for the apparatus of FIG. 1.
Figure 6A:
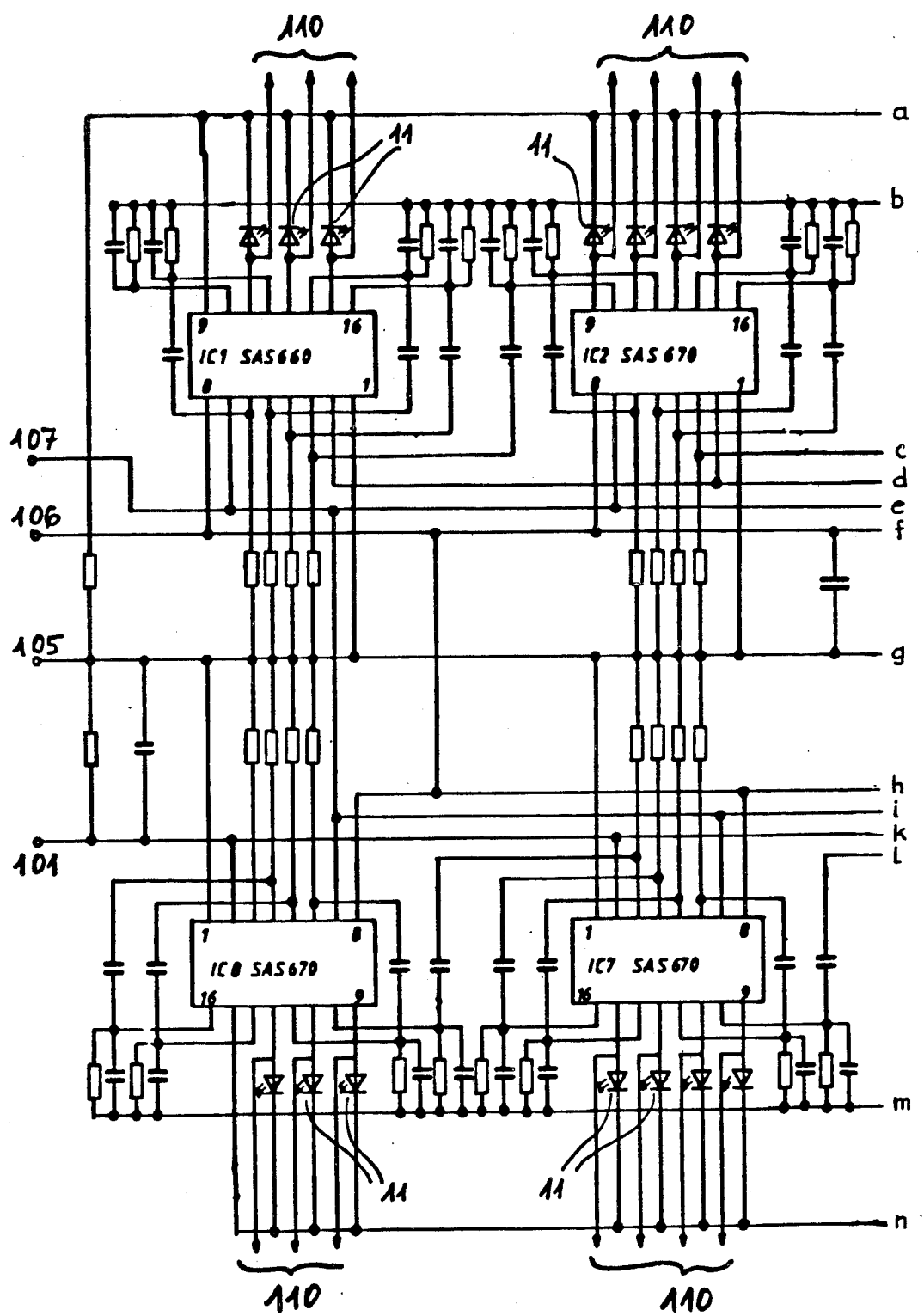
FIGS. 6A and 6B illustrate a circuit schematic of a counter unit together with controlling amplifiers for the apparatus of FIG. 1.
Figure 6B:
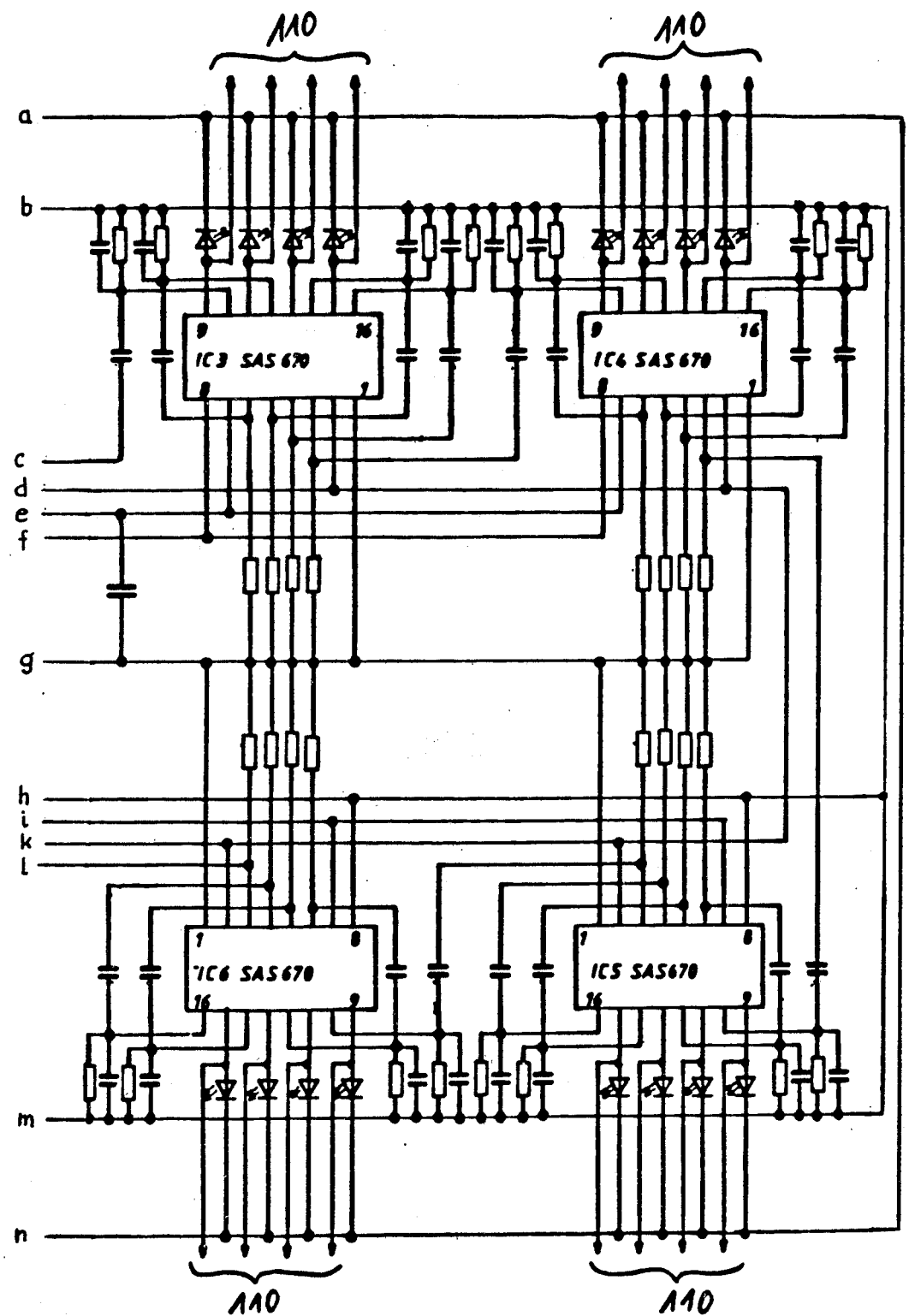

FIG. 4 shows a switching amplifier, thirty of which are provided for driving the thirty heating elements 15. Inputs 110 of each switching amplifier is connected to the corresponding output 110 of the counter (FIG. 6). Depending on the state of the counter, one of the switching amplifiers receives an impulse via its terminal 110, which impulse fires thyristor 53 via transistors 51 and 52 if it is not short-circuited by transistor 50. The time-constant of capacitor 57 and resistor 58 is so dimensioned that thyristor 53 will be conductive for a period of 2.5 seconds.

Figure 5:
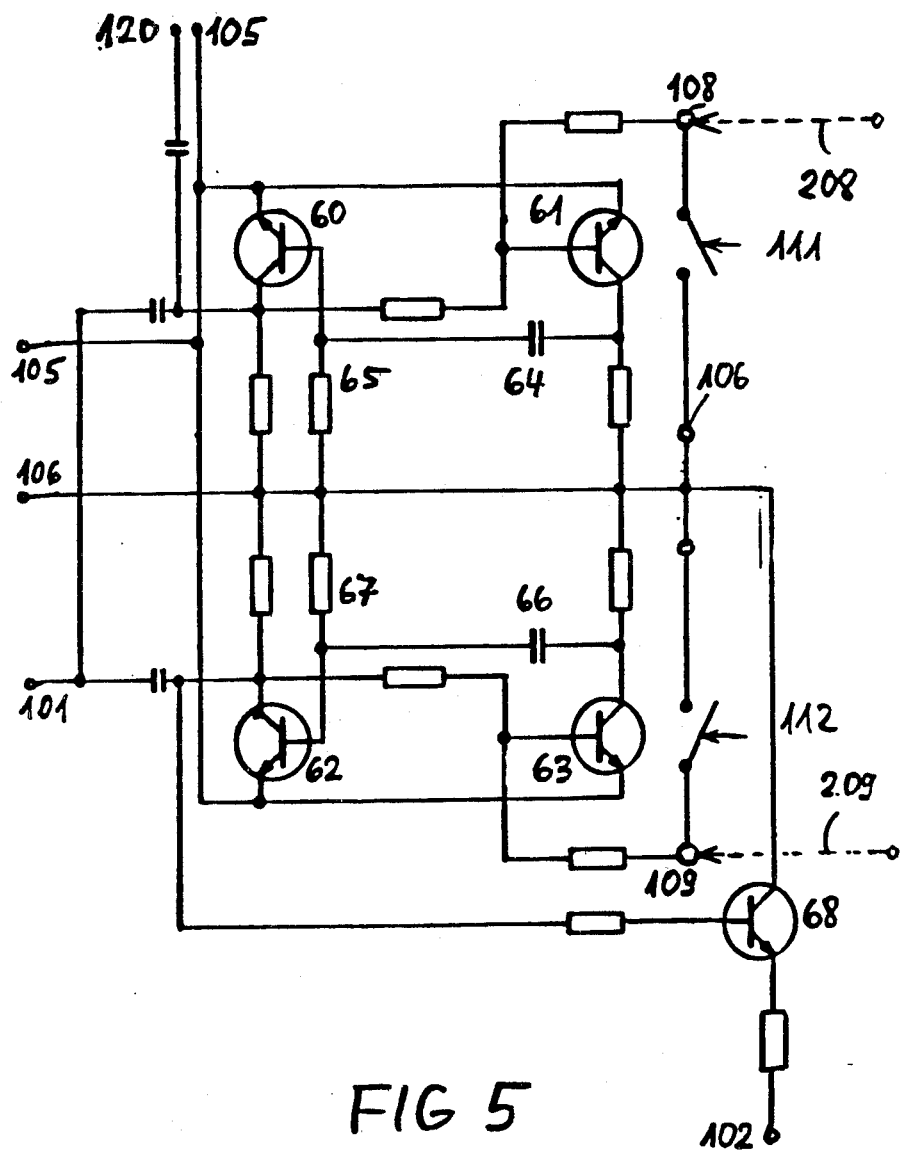
FIG. 5 is a circuit diagram for a pulse generator for the apparatus of FIG. 1.

FIG. 5 shows an arrangement of two pulse generators for deriving defined control pulses (contact bounce suppression) for the counter (FIG. 6) from the actuation of the positive switch 21 (contact 111) or the negative switch 22 (contact 112), respectively. Each pulse generator comprises two transistors 60,61 or 62,63 that are connected in monoflop fashion to provide an output pulse of 0.5 seconds duration at the collector of transistor 60 or 62, if triggered by the closing of the corresponding switch 111 or 112. These pulses flow via a coupling capacitor to terminal 101 leading to the counter (FIG. 6).

If the positive switch (contact 111) is actuated a counting pulse flows via terminal 101 to the counter. Simultaneously a signal flows from the appropriate counter output to the corresponding switching amplifier (input 110) so that thyristor 53 energizes the corresponding heating element for 2.5 seconds. If the negative switch (contact 112) is actuated a counting pulse is also fed via terminal 101 to the counter. At the same time, however, transistors 68 and 50 (FIG. 4) become conductive, whereby the signal at terminal 110 of the switching amplifier (FIG. 4) is short-circuited and the corresponding thyristor 53 will not become conductive. The switching amplifier and the heating element 15 corresponding to this counter state will thus not be energized.

The counter shown in FIG. 6 comprises eight integrated counter circuits IC1 to IC8. The integrated circuit IC1 is of the type Telefunken SAS 660 and the others are of the type Telefunken SAS 670. The circuit IC1 (SAS 660) is of such configuration that upon switching on the supply voltage the whole counter is set into its starting position in which none of the thirty LEDs 11 connected to the outputs is energized. In this position none of the thirty outputs 110 provide a signal. Each counting pulse fed to terminal 101 (actuation of positive switch 111 or negative switch 112) advances the counter by one position so that the corresponding LEDs 11 will be energized one after the other.

The whole arrangement functions as follows: The counter (FIG. 6) is in its starting position when the apparatus is switched on. Each actuation of a switch 21 (contact 111) or 22 (contact 112) advances the counter into the following position, whereby the thirty switching amplifiers (FIG. 4) will receive signals one after the other and the respective working states will be indicated by the corresponding LED 11. If the positive switch was actuated the corresponding heating element 15 is energized at the same time and prints a mark 32 on registration carrier 30. If the negative switch was actuated the signals at inputs 110 of the switching amplifiers are short-circuited by transistor 50 so that the heating element 15 corresponding to the respective counting position is not energized.

Terminal 120 shown in FIG. 5 is provided to deliver counting pulses to calculator 17 (FIG. 1). At each actuation of the positive switch 21 (contact 111) a pulse is delivered from the collector of transistor 60 to the calculator so that at the conclusion of the operation the calculator will have added up the number of positive findings.

FIG. 7 shows a schematic view of a display tableau 200 that can be connected to the basic apparatus shown in FIGS. 3 to 6. Thirty lamps 201 are placed at the interdental positions of a dentition diagram preferably arranged in the form of a broad and laughing mouth in a face that is well-known to children. The lamps will be switched on simultaneously when the corresponding heating elements 15 are energized.

Figure 10:
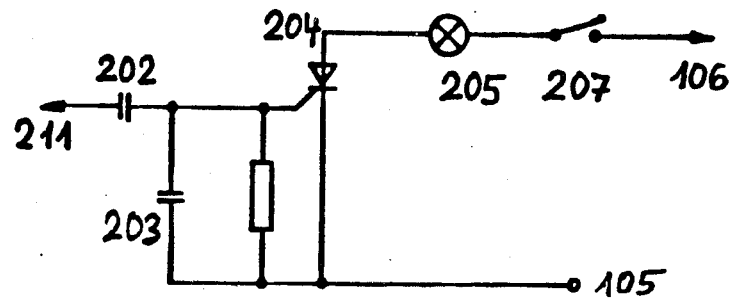
FIG. 10 is a circuit diagram for a display driver for a tableau according to FIG. 7.

FIG. 10 shows a switching circuit as provided for each such lamp. Input 211 is connected to the switching amplifier (FIG. 4, dotted connection 211) and triggers a thyristor 204 if an appropriate signal is present at capacitor 57 (FIG. 4). The lamp 205 will be lit and this state will be stored until the supply voltage of thyristor 204 is interrupted by a reset switch 207. On completion of a full examination procedure the lighting up of the energized lamps (film existing on tooth) will demonstrate impressively to the patient the state of his dental hygiene.

Figure 11:
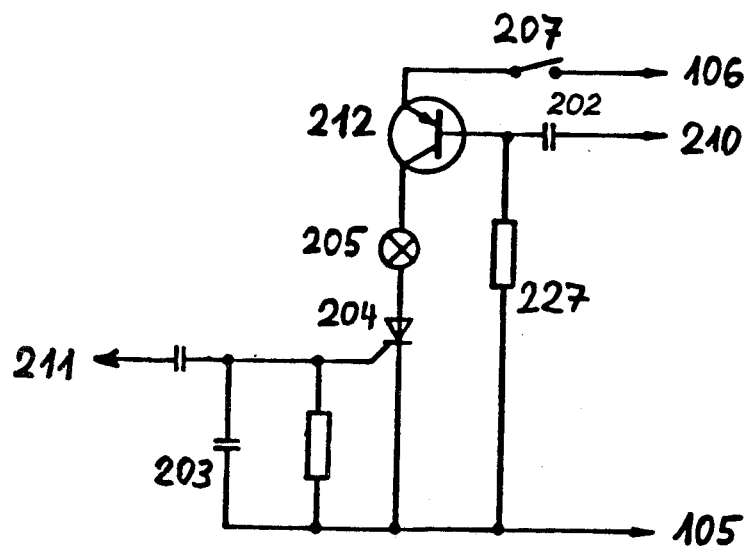
FIG. 11 is a circuit diagram for a further embodiment of a display driver.

FIG. 11 shows an an alternative embodiment for of the switching circuit of FIG. 10 in which the examination result of a preceding examination can be overwritten by the results of a new examination. The results of the preceding examination can be stored in a store by means of a code card and read into the apparatus according to the invention for demonstration to the patient before the subsequent examination is begun. Lamps going out or new ones lighting up make it possible to visually observe an improvement or a deterioration of the new findings.

The function of the switching circuit of FIG. 11 is as follows: Controlled from a storage means all thyristors 204 conductive during the first examination are fired again, so that the first findings are shown on the display tableau. In order to enable the erasure of the state of all thyristors after each new finding, the supply line is connected via a transistor 212 which is held normally in conductive state by a resistor 227. An erase pulse (of approximate 0.2 seconds duration) is fed via capacitor 202 to transistor 212 from terminal 210 (dotted line in (FIG. 4) when the counter (FIG. 6) reaches the position allocated to the corresponding switching amplifier. In the case of a positive finding a firing pulse of longer duration than the erase pulse is fed to input 211 so that the thyristor again energizes the corresponding lamp 205. In the case of negative finding, no signal appears at input 211 so that thyristor 204 is not fired again. The capacitor 203 serves to suppress interference pulses of short duration.

FIG. 8 shows a sensor head 220 having two sensor surfaces 221 and 222. In the case of a positive finding the gum of the patient is touched with the sensor surface 221 below the corresponding interdental space; in the case of a negative finding the sensor surface 222 is touched by the finger of the examining person. Each of these two sensor surfaces 221 and 222 is connected to input 225 of an AF amplifier (FIG. 9) that is biased into a linear working region by a series resistor 224. When input 225 is touched, a hum voltage is developed at the output 226. One amplifier each (FIG. 9) is connected to terminals 108 and 109 of the pulse generator (dotted lines 208 and 209 in FIG. 5) instead of the input switches 111 and 112, which amplifiers trigger the corresponding monoflop when a sensor surface is touched. The preamplifiers (FIG. 9) can be integrated in the sensor head.

Figure 12:
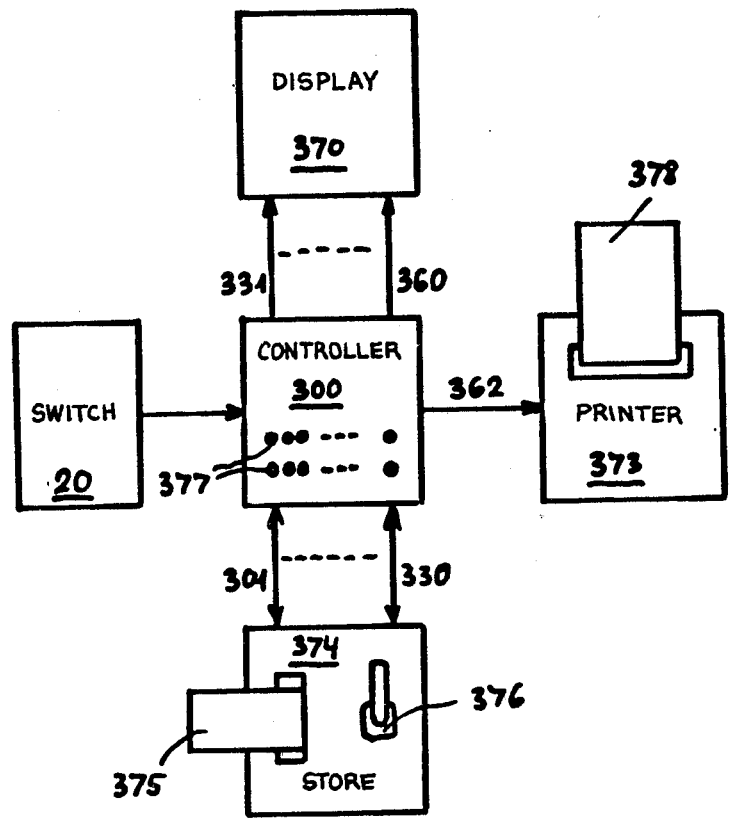
FIG. 12 is a block diagram for an improvement of the invention with a storage means and a printer.

The block diagram of FIG. 12 shows a further version of the present invention. A control unit 300, together with a printer 373, perform similar tasks as the registration apparatus 10 of FIG. 1. The control unit contains also a field of LEDs 377 to indicate the various examination positions. Instead of the registration field 13 and the heating elements 15, a printer 373 is provided that is controlled via a cable 362 from the control unit in such a way that it prints the findings for the individual dentition positions in spatial correspondence onto a dentition diagram provided on an output paper 378.

The control unit can similarly control a display tableau (as seen in FIG. 7) to give, parallel to the printout, a visual demonstration of the findings.

Via leads 301 to 330 there is connected to the control unit 300 a store means 374 by which the various findings can be stored in well-known manner on a magnetic card 375. To do this the mode selector 376 is switched to "WRITE". The magnetic or coding card can be kept in a patient's file and is available for subsequent examination. At such follow-up examinations the magnetic card is loaded into the store means 374 and the selector 376 switched to "READ". Now the data of the findings stored on the magnetic card 375 are read out and furnished via the control unit 300 to the display tableau 370. The previous findings thus made visible may then be overwritten by the new findings as explained in connection with FIGS. 7 and 11.

The magnetic card can have a plurality of storage tracks, each of which can be used to store the findings of one examination. In this way the results of several examinations can be selectively read out and demonstrated on the tableau.

Although the description has so far mainly referred to the Approximal Space Plaque Index (API) where all interdental spaces are evaluated for positive or negative results, it is, of course, also possible to use the invention for other evaluation methods.

Furthermore it is not absolutely necessary to allocate the examination results to the interdental spaces, they may also relate to the different tooth positions themselves in the dentition diagram.

As printer 373 is equipped to print a great variety of different characters or signs (contrary to the thermal registration apparatus of FIG. 1 having simple heating elements 15), it is of course also possible to print signs like "+" or "−" directly at the appropriate spatial positions of the dentition diagram. It is moreover possible to print not only two different examination results like "positive" or "negative", but practically any number of different findings. To establish a plaque index according to the Quigley-Hein method, for example, it is necessary to give the individual tooth a grade. In addition to the finding "0", five additional result grades have to be represented; this can easily be achieved with a printer 373 by printing the figures 0 to 5. It is evident that in this way any number of graded examination results can be represented.

For the determination of the plaque index according to Silness-Löe not all interdental spaces are graded, but four surfaces of selected teeth at a time, and the spatial representation of the dentition diagram in the registration apparatus must be adapted accordingly.

We claim:

1. An apparatus for recording and evaluating a number of dental findings each corresponding to a respective one of a given number of dental examination positions, said apparatus comprising:

a marking carrier imprinted with a dental scheme indicating the location of each examination position;

a marking device including a number of marking elements each arranged to correspond to a respective one of the examination positions for marking said marking carrier;

an input device for producing two different switching instructions each corresponding to a different dental finding;

a counter connected to receive the two different switching instructions from said input device, said counter having a plurality of counter outputs each corresponding to a respective one of the examination positions and said counter being operative to switch over an enabling signal from one said counter output corresponding to one examination position to a next counter output corresponding to the next examination position in the dental scheme upon receipt by said counter of either of said two different switching instructions;

a plurality of switching amplifiers each connecting a respective one of said counter outputs to a respective one of said marking elements corresponding to the same examination position as said respective counter output, wherein the switch over of the enabling signal to said next counter output enables the switching amplifier corresponding to the examination position associated with said next counter output, and each said switching amplifier includes exciting means responsive to said input device for causing that switching amplifier, when enabled by said counter, to excite the corresponding marking element unless a given one of said two different switching instructions is produced by said input device.

2. An apparatus as defined in claim 1, wherein said marking carrier is heat sensitive paper, said marking elements are heated elements spatially arranged to correspond to the location of the examination positions indicated by the dental scheme imprinted on said heat sensitive paper, said marking device is constructed to mount said heat sensitive paper above said heating elements, and the enabled switching amplifier excites the heating element associated with said enabled switching amplifier for a short time when said given one of the two different switching instructions is produced by said input device.

3. An apparatus as defined in claim 1, and further comprising a display device having a number of display elements corresponding to the given number of examination positions, said display elements being spatially arranged according to the location of examination positions indicated by the dental scheme and said display device being connected to said counter so that said display elements are actuated in succession with every switching instruction to display the respective examination positions.

4. An apparatus as defined in claim 3, wherein said display elements are lamps.

5. An apparatus as defined in claim 4, wherein said lamps are light emitting diodes.

6. An apparatus as defined in claim 1, wherein said input device is a foot switch including two switching contacts for furnishing the two different switching instructions.

7. An apparatus as defined in claim 1, and further comprising a calculating means including a display and connected for receiving and making a first count of all switching instructions and and making a second count of only the given one of said two different switching instructions, said calculating means including means for forming a quotient of said first and second counts and displaying said quotient on said display.

8. An apparatus as defined in claim 7, wherein said input device includes a pulse generator for producing a pulse corresponding to the given one of said two different switching instructions, and said calculator comprises a pocket calculator having a percent key and which adds the pulses corresponding to the given one of said two different switching instructions.

9. An apparatus as defined in claim 1, and further comprising a display tableau having a carrier panel with display lamps arranged on said carrier panel to correspond with the location of the examination positions indicated by the dental scheme imprinted on said marking carrier, said lamps each being connected to be switched on in correspondence to the given one of said two different switching instructions.

10. An apparatus as defined in claim 9, wherein said display lamps are arranged to be uniformly spaced from each other on said carrier panel and to delineate an overdimensionally drawn dental scheme.

11. An apparatus as defined in claim 9, and further comprising a lamp circuit associated with each display lamp; display drivers each coupled to a respective one of said display lamp circuits and to a respective one of said switching amplifiers, said display drivers each having memory means for maintaining energization of said display lamps after termination of the enabling signal; and a common interrupting switch connected in series with all said lamp circuits for disconnecting said display lamps.

12. An apparatus as defined in claim 11, and further comprising interrupting transistors each connected in a respective one of said lamp circuits for blocking said lamp circuit for a short duration if a new dental finding is to be displayed.

13. An apparatus as defined in claim 1 wherein said input device comprises a finger operated switch having two switch contacts each for producing a respective one of said two different switching instructions.

14. An apparatus as defined in claim 13, wherein said finger operated switch comprises a sensor pen having a sensor tip for producing a first switching pulse corresponding to one of said two different switching instructions and a sensor plate disposed on the circumference of said sensor pen for producing a second switching pulse corresponding to the other of said two different switching instructions.

15. An apparatus as defined in claim 14, wherein said sensor pen includes first and second low frequency amplifiers each having an output and each connected to receive an input from a respective one of said sensor tip and said sensor plate, said first low frequency amplifier delivering a switching pulse to its output when said sensor tip is touched, and said second low frequency amplifier delivering a switching pulse to its output when said sensor plate is touched.

* * * * *